United States Patent [19]

Wenzel et al.

[11] Patent Number: 4,711,894

[45] Date of Patent: Dec. 8, 1987

[54] STABILIZED TOCOPHEROL IN DRY, PARTICULATE, FREE-FLOWING FORM

[75] Inventors: Bruce E. Wenzel, Bloomington; James P. Clark, Richfield, both of Minn.

[73] Assignee: Henkel Corporation, Ambler, Pa.

[21] Appl. No.: 819,779

[22] Filed: Jan. 16, 1986

[51] Int. Cl.$^4$ ............................................. A61K 31/355
[52] U.S. Cl. ..................................... 514/458; 514/970
[58] Field of Search ................................ 514/458, 970

[56] References Cited

U.S. PATENT DOCUMENTS

| | | | |
|---|---|---|---|
| 3,608,083 | 9/1971 | Bunnell et al. | 514/458 |
| 3,873,694 | 3/1975 | Kanig | 514/458 |
| 4,395,422 | 7/1983 | Schmidt et al. | 514/458 |

FOREIGN PATENT DOCUMENTS

| | | | |
|---|---|---|---|
| 132821 | 2/1985 | European Pat. Off. | 514/970 |
| 53-148546 | 12/1978 | Japan | 514/458 |
| 56-164749 | 12/1981 | Japan | 514/458 |

*Primary Examiner*—Douglas W. Robinson
*Attorney, Agent, or Firm*—Ernest G. Szoke; Patrick J. Span

[57] ABSTRACT

A dry, particulate, free-flowing form of Vitamin E (α-tocopherol) is provided which includes a potency stabilizer for the Vitamin E. The potency stabilizers are hydroxy acids or amino acids such as ascorbic acid, citric acid, methionine and cysteine.

8 Claims, No Drawings

STABILIZED TOCOPHEROL IN DRY, PARTICULATE, FREE-FLOWING FORM

BACKGROUND OF THE INVENTION

1. Field of the Invention

This invention relates to potency stabilized tocopherol in a dry, particulate, free-flowing form. The stabilized products are in the form of powders or fine granules in which a carrier supports the tocopherol, whose potency is stabilized with certain acid compounds.

2. Statement of Related Art

Vitamin E comprises a group of natural substances known as tocopherols. These are fat soluble, closely related chemical compounds found in vegetable oils such as wheat germ oil, soy bean oil and the like. Alpha-tocopherol has the greatest biological activity while its homologs have Vitamin E activity to a lesser extent. The tocopherols and their esters are normally water insoluble, oily, waxy or low-melting, which properties generally make them unsuitable for certain pharmaceutical applications, particularly those in which a powder is required such as in tablets or capsules.

In recent years, efforts have been to convert various vitamin products, including Vitamin E, to a free-flowing, high density agglomerated composition. Illustrative thereof are U.S. Pat. Nos. 3,914,430; 3,947,596; 3,959,472; and 3,962,384 assigned to Hoffman-La Roche, Inc., which are all based on U.S. patent application Ser. No. 242,789, filed Apr. 10, 1972 and now abandoned. In general, these patents disclose a spray drying process for preparing free-flowing, high density agglomerates which are suitable for compression into tablets. In these patents, hydrolyzed gelatin and/or other ultra-fine absorbents are employed as a carrier for the vitamin. In order to ensure the desired stability of Vitamin E activity in the final powder it is preferred to use the tocopherol esters.

In U.S. Pat. No. 3,608,083, also assigned to Hoffman-La Roche, there is disclosed another spray drying method for producing a Vitamin E powder with good pelleting characteristics for incorporation into tablets and capsules. The powders are composed of a Vitamin E active compound and carried by a gelatin hydrolysate having a molecular weight of about 9,000 to about 10,000 and a zero Bloom. In Example 3 a multi-vitamin tablet containing Vitamin C (ascorbic acid) and Vitamin A along with Vitamin E is formulated. The powders are prepared by a spray drying process.

U.S. Pat. No. 3,869,539, assigned to A/S Ferrosan, discloses a method of preparing a dry, particulate, free-flowing form dispersible in cold water of fat-soluble vitamins including Vitamin E. In this method, the vitamins are incorporated in a finely dispersed form in a mass of gelatin. In discussing prior methods of forming such products from gelatin, it is disclosed that the aqueous gelatin solutions must be initially treated with ascorbic acid or mixtures thereof with citric acid, or a mixture of citric acid and sorbose. This treatment method, however, is noted as suffering from various drawbacks and the invention disclosed in U.S. Pat. No. 3,869,539 is a method of avoiding such drawbacks through using a mass of gelatin partially decomposed with a base or an inorganic acid, which is then neutralized to a pH value between 4.5 and 7.

In a series of U.S. Pat. No. 4,395,422; 4,262,017; 4,486,435, assigned to B.A.S.F. Wyandotte Corporation, there is disclosed spray dried Vitamin E powders utilizing hydrolyzed gelatin and caseinates. The use of flow improvers, such as synthetic silica are also disclosed. In U.S. Pat. No. 4,486,435, hydrophobic silica is employed.

Mixtures of Vitamin E and certain acids have been studied for use as anti-oxidants to protect various materials such as lard and vegetable oils, fatty acids, sardines and arachidonic acid. These studies can be seen from the following literature:

(a) "Interaction of Galvinoxyl Radical with Ascorbic Acid, Cysteine, and Glutathione in Homogeneous Solution and in Aqueous Dispersions." J. Tsuchiya, T. Yamada, E. Niki, and Y. Kimiya, BULL. CHEM. SOC. JAPAN, 1985, 58(1), 326–30.

(b) "Studies on the Activities of Natural Anti-oxidants (Part 3). Preventing Effects of Natural Anti-oxidants on Oxidation of Dried Sardine". K. Nishikawa, H. Oka, and T. Yasuda, KENYU-HOKOKU-EHIME-KEN KOGYO GIJUTSU 1984, 22, 15–20.

(c) "Arachidonic Acid Anti-oxidation in an Aqueous Media Effect of $\alpha$-tocopherol, Cysteine and Nucleic Acids". B. Bozin, J. Cillard, J. P. Kaskas, and P. Cillard, JAOCS, 1984, 61, 1212–1215.

(d) "Some Effects of Amino Acids and Certain Other Substances on Lard Containing Phenolic Anti-oxidants". D. F. Clausen, W. O. Lundberg, and G. O. Burr, JAOCS, 1947, 24, 403–404.

In forming such dry, free-flowing Vitamin E compositions, however, a loss of potency has been recognized. It is important and desirable that the Vitamin E powders contain and maintain a high potency in use.

BRIEF SUMMARY OF THE INVENTION

It has now been discovered that certain acid compounds will stabilize the potency of Vitamin E compounds when processed into a dry particulate free-flowing form. While certain acids have been used a secondary anti-oxidants along with tocopherol compounds, it has not been recognized, however, that such acid compounds are a potency stabilizer for the Vitamin E itself. Accordingly, the present invention is concerned with a potency stabilized composition in a dry, particulate, free-flowing form which is comprised of Vitamin E incorporated in a carrier whose potency has been stabilized with an effective amount of a certain acid compound. Such potency stabilizing acid compounds are hydroxy acids or amino acids, such as citric acid, ascorbic acid, methionine and cysteine. Citric acid and ascorbic acid have been found to be the most desirable of these acids when employed alone. In admixture with the other amino acids, ascorbic acid with methionine or cysteine is preferred.

DETAILED DESCRIPTION AND PREFERRED EMBODIMENTS

As indicated, the present invention concerns itself with dry, particulate, free-flowing forms of Vitamin E which are comprised of the active tocopherol compound, a carrier for such tocopherol and a potency stabilizing acid compound employed in an effective amount to stabilize the potency of the tocopherol in the composition.

The Vitamin E active composition is the free tocopherol form. The present invention finds particular utility with the tocopherols which are available in a liquid, oily form. The invention is applicable to natural Vitamin E in which the active Vitamin E compound is d-$\alpha$- tocopherol as well as synthetic Vitamin E in which d,l-α-tocopherol is present. In addition to the most active α-form there may also be present other homologs such as the beta, gamma, delta and other forms which have Vitamin E activity to a lesser extent. In general, compositions in which the α-tocopherol is present in excess of 85% and preferably in excess of 90%, will be employed in this invention. The compositions may contain in addition to the Vitamin E, carrier and potency stabilizer acid compound, additional fillers and flow additives to maintain the particulate free-flowing form of the composition.

The potency stabilizing acid compounds contemplated by the present invention are various hydroxy acids and amino acids. Hydroxy- and amino acids containing from 3 to 6 carbon atoms are particularly desirable. Such hydroxy acids include ascorbic acid and citric acid. The amino acids which find utility are methionine and cysteine, which also contain a sulfur atom. Of these acids, ascorbic acid is preferred when employed alone, with citric, cysteine and methionine following in descending order. Where mixtures of the acids are employed, it is preferred that ascorbic acid mixed with citric acid or cysteine.

In regard to the carriers into which will be incorporated the tocopherol compound and the potency stabilizer acid compound are those generally shown in the references discussed earlier. Such carriers will include gelatin, silica gel and various starches or gums. Some carriers will also act as flow control agents or such may be incorporated along with the other carriers. Examples of such materials are silicic acid, silicon dioxide, various silicates and silico-aluminate (Zeolite). Food grade organic carriers include carbohydrates including gums such as gum Acacia, maltodextrin, as well as gelatin sugar matrixes.

Based on a weight of Vitamin E active compound and carrier, the composition would comprise from about 20 to about 60% of the Vitamin E active compound and 40 to 80% of a carrier. Based on the amount of active Vitamin E compound, the potency stabilizing acid would be employed in amount of from about 2 to about 50% by weight and preferably from 10 to 50% based on the weight of the total amount of tocopherol compound and stabilizer present in the composition. Thus, the weight ratio of tocopherol to stabilizer will be on the order of 98:2 to about 1:1, with about 2:1 to 1.5:1 being preferred.

The compositions of the present invention will be prepared in the same manner as the compositions described earlier which the tocopherol compound, the potency stabilizer and the carrier will be formed into an emulsion or slurry and spray dried. The emulsion or slurry will be made up to provide a proper spray viscosity to form a product which has a particle size in the range of from below 70, i.e. down to 20-40 microns up to about 900 microns, preferably about 200-500 microns.

To further illustrate the various objects and advantages of the present invention, the following examples are provided. It is understood that their purpose is entirely illustrative and in no way intended to limit the scope of the invention.

EXAMPLE 1

Samples were prepared by coating 6 grams of d-α-tocopherol (>88% purity) and 1.5 grams of stabilizer candidates on 30 grams silica gel (60-200 mesh) using a laboratory rotary evaporator. After preparation, these were stored in a refrigerator (4° C.) for control and in the hot room (49° C.). After one month, samples were taken from both places and analyzed for weight percent alpha-tocopherol. Likewise, after 2 months storage, the remaining set was sent in for analyses. The stability was determined by calculating relative change:

$$\text{Relative Change (\%)} = \frac{toc\ 49°\ C. - toc\ 4°\ C.}{toc\ 4°\ C.} \times 100 \quad \text{(Equation 1)}$$

Results for the relative change are given in Table I. The data show ascorbic acid is best with citric acid being very close for retarding loss of potency, when comparing these to the control to which no stabilizer was added.

TABLE I

| | RELATIVE CHANGE IN D-ALPHA TOCOPHEROL CONTENT | | | | |
|---|---|---|---|---|---|
| Storage Time | Control | Citric Acid | Ascorbic Acid | Methionine | Cysteine |
| 1 month | −20% | −8 | −2 | −14 | −14 |
| 2 months | −93 | −13 | −6 | −80 | −65 |

EXAMPLE 2

The preparation of samples involved the same weights of materials as Example I. The differences were, first, a narrower and more coarse mesh (35-60 mesh) silica gel was used for the matrix. Second, solvent and water were removed with a vacuum of <0.1 mmHg by means of an oil pump. Third, after drying under vacuum was complete, the samples were cooled down and vacuum broken with nitrogen rather than air.

Samples were stored both at 4° C. and 49° C., as before. A storage temperature pair of each preparation were removed for analysis after one month and again after two months. The stability was determined by calculating the change in d-alpha-tocopherol relative to 4° C. (Equation 1). Results are given in Table II.

TABLE II

| | RELATIVE CHANGE IN D-ALPHA-TOCOPHEROL CONTENT | | | | |
|---|---|---|---|---|---|
| Storage Time | Control | Citric Acid | Ascorbic Acid | Methionine | Cysteine |
| 1 month | −47 | −30 | +0.8 | −8 | −42 |
| 2 months | −53 | −39 | −9.4 | −29 | −42 |

EXAMPLE 3

This example was conducted to determine:
(a) which stabilizer best prevents potency loss;
(b) the concentration level to accomplish the result; and
(c) the effects of a mixture of two stabilizers acting together.

The constraints were: first, a constant ratio of tocopherol stabilizer coating to the silica gel matrix of 7.5:30, therefore 20% loading; and second, the concentration ranges of the tocopherol compound and stabilizers were: 50-100% (or 3.75 to 7.5 g) for the tocopherol compound and 0-50% (0 to 3.75 g) for the stabilizers.

The preparation of samples using the same materials was the same as for Example II above, thus 7.5 g of the tocopherol compound alone or with stabilizer(s) were coated on 30 g of silica gel. This was accomplished by first dissolving the tocopherol and stabilizers in a 50/50 mixture of isopropyl alcohol/methanol. Next the solution plus the silica gel (35–60 mesh) were put in a round bottom flask and solvent removed by pulling vacuum (<0.1 mmHg) while rotating in a warm water bath. After drying under vacuum was complete, the samples were cooled down while still under vacuum. The vacuum was broken with nitrogen rather than air. The dried sample preparations were scraped from the flask and mixed thoroughly to be homogeneous. Details as to the composition of the samples can be seen from Table IIIA below.

Samples of each of the 27 preparations were stored both at 4° C. and 49° C. After two months all samples were removed and analyzed for d-alpha-tocopherol content. The results are shown in Table IIIB below, in which the samples are arranged in order of increasing % loss, which was calculated from the relative change at the two storage temperatures by the following formula:

$$\% \text{ loss} = \left[ \frac{toc\ 4°\ C. - toc\ 49°\ C.}{toc\ 4°\ C.} \right] \times 100 \quad \text{(Equation 2)}$$

TABLE III A

| Run Order | d-α-tocopherol | Citric Acid | Ascorbic Acid | Methionine | Cysteine |
|---|---|---|---|---|---|
| 1 | 50 | 0 | 0 | 25 | 25 |
| 2 | 50 | 50 | 0 | 0 | 0 |
| 3 | 100 | 0 | 0 | 0 | 0 |
| 4 | 50 | 25 | 0 | 0 | 25 |
| 5 | 90 | 10 | 0 | 0 | 0 |
| 6 | 50 | 0 | 25 | 0 | 25 |
| 7 | 100 | 0 | 0 | 0 | 0 |
| 8 | 70 | 7.5 | 7.5 | 7.5 | 7.5 |
| 9 | 70 | 0 | 30 | 0 | 0 |
| 10 | 50 | 25 | 0 | 25 | 0 |
| 11 | 50 | 25 | 0 | 25 | 0 |
| 12 | 90 | 0 | 0 | 0 | 10 |
| 13 | 50 | 0 | 25 | 0 | 25 |
| 14 | 50 | 25 | 25 | 0 | 0 |
| 15 | 50 | 0 | 25 | 25 | 0 |
| 16 | 70 | 30 | 0 | 0 | 0 |
| 17 | 50 | 0 | 25 | 25 | 0 |
| 18 | 50 | 0 | 50 | 0 | 0 |
| 19 | 50 | 0 | 0 | 25 | 25 |
| 20 | 50 | 0 | 0 | 50 | 0 |
| 21 | 50 | 0 | 0 | 0 | 50 |
| 22 | 70 | 0 | 0 | 30 | 0 |
| 23 | 70 | 7.5 | 7.5 | 7.5 | 7.5 |
| 24 | 90 | 0 | 10 | 0 | 0 |
| 25 | 50 | 25 | 0 | 0 | 25 |
| 26 | 70 | 0 | 0 | 30 | 0 |
| 27 | 70 | 0 | 0 | 0 | 30 |

TABLE III B

ANALYTICAL RESULTS AFTER TWO MONTHS STORAGE

| Run Order | Wt % 4° C. | α-tocopherol 49° C. | % Loss |
|---|---|---|---|
| 13 | 6.70 | 6.50 | 2.9 |
| 4 | 7.60 | 6.90 | 9.2 |
| 18 | 8.00 | 7.10 | 11.2 |
| 6 | 7.70 | 6.80 | 11.7 |
| 14 | 7.5 | 6.40 | 14.7 |
| 17 | 8.30 | 7.00 | 15.7 |
| 22 | 10.30 | 8.60 | 16.5 |
| 8 | 11.10 | 9.10 | 18.0 |
| 9 | 13.30 | 10.70 | 19.5 |
| 20 | 7.80 | 6.20 | 20.5 |
| 15 | 8.60 | 6.70 | 22.1 |
| 5 | 13.40 | 10.30 | 23.1 |
| 2 | 7.10 | 5.30 | 25.4 |
| 23 | 12.10 | 9.00 | 25.6 |
| 24 | 14.90 | 10.70 | 28.2 |
| 19 | 7.40 | 5.30 | 28.4 |
| 23 | 15.20 | 10.80 | 28.9 |
| 1 | 7.00 | 4.90 | 30.0 |
| 16 | 10.70 | 7.40 | 30.8 |
| 25 | 6.40 | 4.20 | 34.4 |
| 27 | 11.70 | 7.60 | 35.0 |
| 11 | 6.40 | 3.80 | 40.6 |
| 3 | 15.40 | 9.0 | 41.6 |
| 7 | 16.40 | 9.20 | 43.9 |
| 26 | 14.50 | 8.00 | 44.8 |
| 21 | 6.80 | 3.70 | 45.6 |
| 10 | 7.50 | 1.40 | 81.4 |

The foregoing shows that as a single stabilizer alone, ascorbic acid best prevents potency loss, i.e. Runs 18 and 6. In mixtures of stabilizer, a mixture of ascorbic acid and cysteine (Run 13) followed by a mixture of cysteine and citric acid (Run 4) followed in order.

We claim:

1. In a dry, potency stabilized, particulate, free-flowing tocopherol composition of a carrier and a tocopherol compound, the improvement wherein said tocopherol compound is d- or d,l-alpha-tocopherol and said composition contains a potency stabilizer selected from the group consisting of ascorbic acid, a mixture of ascorbic acid and cysteine and a mixture of citric acid and cysteine said potency stabilizer being present in an amount of about 2–50% by weight based on the total weight of tocopherol and stabilizer and wherein the weight ratio of tocopherol to stabilizer is from 98:2 to about 1:1.

2. A composition as defined in claim 1 wherein said stabilizer is present in an amount of 10–50%.

3. A composition as defined in claim 1 wherein the weight ratio of tocopherol to stabilizer is about 1.5:1 to 2:1.

4. A dry, potency stabilized, particulate, free-flowing tocopherol composition comprising about 20–60% by weight of d- or d,l-alpha-tocopherol, about 40–80% by weight of carrier based on a total weight of carrier and said tocopherol compound and a potency stabilizer selected from the group consisting of ascorbic acid, a mixture of ascorbic acid and cysteine and a mixture of citric acid and cysteine, said potency stabilizer being present in an amount of about 2–50% by weight based on total weight of stabilizer and tocopherol compound.

5. A composition as defined in claim 4 in which said carrier is selected from the group consisting of hydrolyzed gelatin, silica gel, and carbohydrates.

6. A composition as defined in claim 4 wherein said stabilizer is solely ascorbic acid.

7. A composition as defined in claim 4 wherein said stabilizer is a mixture of ascorbic acid and cysteine.

8. A composition as defined in claim 4 wherein said stabilizer is a mixture of citric acid and cysteine.

* * * * *